United States Patent
Johnston et al.

(10) Patent No.: US 11,278,041 B2
(45) Date of Patent: Mar. 22, 2022

(54) PROCESSES OF TREATING GRAIN

(71) Applicants: The United States of America, as represented by the Secretary of Agriculture, Washington, DC (US); DANISCO US INC., Palo Alto, CA (US)

(72) Inventors: David Johnston, Wyndmoor, PA (US); Jayarama K. Shetty, Pleasanton, CA (US); Bart C. Koops, Zuid Holland (NL)

(73) Assignees: The United States of America, as represented by the Secretary of Agriculture, Washington, DC (US); DANISCO US INC., Palo Alto, CA (US)

( * ) Notice: Subject to any disclaimer, the term of this patent is extended or adjusted under 35 U.S.C. 154(b) by 11 days.

(21) Appl. No.: 16/777,103

(22) Filed: Jan. 30, 2020

(65) Prior Publication Data
US 2020/0163360 A1     May 28, 2020

Related U.S. Application Data

(63) Continuation of application No. 15/469,745, filed on Mar. 27, 2017, now abandoned.
(Continued)

(51) Int. Cl.
*A23K 10/12* (2016.01)
*C12P 19/14* (2006.01)
(Continued)

(52) U.S. Cl.
CPC ............. *A23K 10/12* (2016.05); *A23K 10/14* (2016.05); *A23K 10/30* (2016.05); *B02B 3/00* (2013.01);
(Continued)

(58) Field of Classification Search
None
See application file for complete search history.

(56) References Cited

U.S. PATENT DOCUMENTS

| 6,899,910 | B2 | 5/2005 | Johnston et al. |
| 2005/0009133 | A1* | 1/2005 | Johnston ............ B02B 1/04 435/35 |
| 2015/0299752 | A1* | 10/2015 | Han ..................... C12P 19/04 435/99 |

FOREIGN PATENT DOCUMENTS

WO     01/94608 A1     12/2001

OTHER PUBLICATIONS

Vidal Bernardo C Jr et al: "Protease Treatment to Improve Ethanol Fermentation in Modified Dry Grind Corn Processes", Cereal Chemistry. AACC International Inc. vol. 86, No. 3. (May 1, 2009). pp. 323-328. XP008139488. ISSN: 0009-0352. DOI: 10. 1094/CCHEM-86-3-0323 * p. 324-p. 325; figure 1; table II.
(Continued)

*Primary Examiner* — Amber R Orlando
*Assistant Examiner* — Philip A Dubois
(74) *Attorney, Agent, or Firm* — John Fado; Ariel Atkinson (57) ABSTRACT

Processes of treating grain (e.g., corn), involving milling the grain to produce milled grain wherein the grain germ remains intact in the milled grain, and producing a mixture by mixing the milled grain with water and at least one enzyme selected from the group consisting of protease, alpha amylase, glucoamylase, cell wall degrading enzyme, and mixtures thereof, wherein the pH of the mixture is optionally adjusted to a pH of about 3.5 to about 6.5, and incubating the mixture for about 1 to about 3 hours to produce an incubated mixture.

5 Claims, 9 Drawing Sheets

Related U.S. Application Data

(60) Provisional application No. 62/317,807, filed on Apr. 4, 2016.

(51) Int. Cl.
  *C12P 19/02* (2006.01)
  *C12P 7/10* (2006.01)
  *A23K 10/14* (2016.01)
  *A23K 10/30* (2016.01)
  *B02B 3/00* (2006.01)
  *B02C 11/08* (2006.01)

(52) U.S. Cl.
  CPC ............... *B02C 11/08* (2013.01); *C12P 7/10* (2013.01); *C12P 19/02* (2013.01); *C12P 19/14* (2013.01); *C12Y 304/00* (2013.01); *C12P 2201/00* (2013.01); *Y02E 50/10* (2013.01)

(56) References Cited

OTHER PUBLICATIONS

David B Johnston et al.: Use of Proteases to Reduce Steep Time and SO 2 Requirements in a Corn Wet-Milling Process?? . Cereal Chemistry.vol 78, No. 4, (Jul. 16, 2001). pp. 405-410. XP055622175. p. 406. last paragraph-p. 409. paragraph third; figures 1.2.
EP Search Report dated Sep. 27, 2019.

* cited by examiner

PROCESSES OF TREATING GRAIN

REFERENCE TO RELATED APPLICATION

This is a continuation of application Ser. No. 15/469,745, filed 27 Mar. 2017, which claims the benefit of U.S. Provisional Application No. 62/317,807, filed 4 Apr. 2016, which are herein incorporated by reference in their entirety.

BACKGROUND OF THE INVENTION

Disclosed are processes of treating grain (e.g., corn), involving milling the grain to produce milled grain wherein the grain germ remains intact in the milled grain, and producing a mixture by mixing the milled grain with water and at least one enzyme selected from protease, alpha amylase, glucoamylase, cell wall degrading enzyme, or mixtures thereof, wherein the pH of the mixture is optionally adjusted to a pH of about 3.5 to about 6.5, and incubating the mixture for about 1 to about 3 hours to produce an incubated mixture.

The majority of fuel ethanol plants today currently utilize similar processes to produce Distillers Dried Grains with Solubles (DDGS), some produce liquid carbon dioxide, and most produce post-fermentation corn oil as the only coproducts. Several plants have modified processes to utilize a dry milling fractionation process prior to fermentation for recovery of germ and pericarp fiber. A few plants have wet separation processes that allow the production of a protein rich feed (about 50% protein) with relatively low fiber content as a new coproduct. Most of the other variations are strictly towards process improvements and do not produce additional new coproducts.

Removal of germ and pericarp fiber using a dry milling fractionation process prior to ethanol fermentation has energy saving advantages over the conventional process because the components removed are not wetted before separation and removal. However, the dry fractionation process unfortunately removes some essential nutrients needed for efficient fermentation with the germ fraction and can lose a significant amount of starch if processing is not done properly. The germ is also relatively low in oil concentration ("18%) because it retains these soluble components; additionally, the pericarp fiber is not by itself a particularly valuable co-product.

Wet fractionation processes such as quick germ/fiber or E-Mill processing require relatively more energy for drying but do not lose fermentation nutrients or as much starch relative to dry fractionation (Singh, V., and S. R. Eckhoff, Cereal Chemistry, 73(6): 716-720 (1996); Singh, V., et al., Cereal Chemistry, 82(2): 187-190 (2005); Murthy, G. S., et al., Cereal Chemistry, 83(5): 455-459 (2006); Murthy, G. S., et al., Industrial Biotechnology, 7(4): 298-307 (2011); U.S. Pat. No. 6,899,910). The germ is higher in oil concentration relative to dry milled germ, making it as valuable as germ from the wet milling process. In both germ recovery processes it is essential that the germ is not broken during the milling processes or oil can be lost.

In the dry process, tempering of the kernel (which raises the moisture content of the kernel) prior to grinding in a special mill is required. There are also sizing and air classification steps taken to separate components after grinding. With the existing wet fractionation processes, the whole kernels need to be soaked in water from about 3 to about 12 hours prior to grinding in a toothed disk mill. This keeps the germ from breaking during milling and helps remove endosperm (and starch) from the separated fractions. The hydration also results in the leaching of the soluble components from the germ that aid in fermentation and help concentrate the oil within the germ. The loss of these soluble components during the dry fraction process results in sluggish or stuck fermentations, and has forced plants utilizing dry fractionation to incompletely recover germ and/or to add supplemental nutrients in order to alleviate these problems.

Several processes that combine dry fractionation with wet milling have also been developed (U.S. Pat. Nos. 3,597,274; 4,181,748). The goals of these processes were to isolate starch by first dry milling the corn and then treating all or part of the ground kernel with sulfur dioxide in order to isolate starch. These processes resulted in significant starch losses that would be unacceptable from an economic standpoint if applied in an ethanol process.

Work done in our laboratory on the development of the E-Milling (Enzymatic Wet Milling) process (U.S. Pat. No. 6,566,125; Johnston, D. B., and V. Singh, Cereal Chemistry, 78(4): 405-411 (2001)) showed that the addition of a protease could replace the sulfite chemical processing and release starch for separation. We later expanded on this technology for the development of the germ and pericarp fiber fractionation process (E-Mill) for use with ethanol production that could utilize other enzymes in addition to proteases (Johnston, D. B., et al., JAOCS, 82(8): 603-608 (2005); Singh et al, 2005). With both of these processes, it was necessary to break the corn kernel without disrupting the germ before the enzyme treatment would be effective. This mandated some form of soaking process be utilized prior to grinding with a toothed disc mill. The capital cost of implementing the soaking step is one of the reasons the wet fraction processes have not found broad acceptance. Reduction of the initial capital costs or significant reduction in operating costs could result in broad adoption of wet fractionation technology in the fuel ethanol industry.

We have developed a simplified enzymatic germ and fiber (pericarp and endosperm) recovery process for use in an ethanol production system that could be implemented using less capital relative to the E-Mill or Quick Germ/Fiber processes and surprisingly does not have the significant ethanol loss issues of other processes.

SUMMARY OF THE INVENTION

Disclosed are processes of treating grain (e.g., corn) involving milling the grain to produce milled grain wherein the grain germ remains intact in the milled grain, and producing a mixture by mixing the milled grain with water and at least one enzyme selected from the group consisting of protease, alpha amylase, glucoamylase, cell wall degrading enzyme, and mixtures thereof, wherein the pH of the mixture is optionally adjusted to a pH of about 3.5 to about 6.5 (e.g., 3.5 to 6.5), and incubating the mixture for about 1 to about 3 hours (e.g., 1 to 3 hours) to produce an incubated mixture.

The processes may further involve separating the incubated mixture into germ and a liquid slurry, reducing the particle size of materials in the liquid slurry by grinding, adding yeast and amylase to the liquid slurry and fermenting for about 30 to about 72 hours (e.g., 30 to 72 hours), removing ethanol from the liquid slurry (e.g., by distillation) and separating (e.g., screening) the liquid slurry into fiber and a defibered liquid slurry, and separating (e.g., centrifuging) the defibered liquid slurry to produce protein solids.

The process may further involve separating the incubated mixture into germ and a liquid slurry, reducing the particle size of materials in the liquid slurry by grinding, adding amylase to the liquid slurry to hydrolyze the starches in the liquid slurry, and separating (e.g., screening) the liquid slurry into fiber and a defibered liquid slurry, and separating (e.g., centrifuging) the defibered liquid slurry into protein solids and a solution containing sugars.

The process may further involve separating the incubated mixture into germ and a liquid slurry, reducing the particle size of materials in the liquid slurry by grinding, adding amylase to the liquid slurry and heating (e.g. about 60° to about 130° C. (60-130° C.), preferably about 75° to about 105° C. (75-105° C.)) for about 15 min to about 2 hours (e.g., 15 min to 2 hours) (liquefaction), adding glucoamylase enzyme to the liquid slurry to hydrolyze the starches in the liquid slurry (saccharification), and separating (e.g., screening) the liquid slurry into fiber and a defibered liquid slurry, and separating (e.g., centrifuging) the defibered liquid slurry into protein solids and a solution containing sugars.

This summary is provided to introduce a selection of concepts in a simplified form that are further described below in the detailed description. This summary is not intended to identify key features or essential features of the claimed subject matter, nor is it intended as an aid in determining the scope of the claimed subject matter.

BRIEF DESCRIPTION OF THE DRAWINGS

FIG. 2C and FIG. 2D are flow charts showing major steps for the degermination process for the production of a sugar solution as described below. FIG. 2C shows the process without thermal gelatinization of the starch, and FIG. 2D shows the process with the thermal treatment and the separate additions of alpha amylase and glucoamylase.

DETAILED DESCRIPTION OF THE INVENTION

Disclosed are processes of treating grain (e.g., corn), involving milling the grain to produce milled grain wherein the grain germ remains intact in the milled grain, and producing a mixture by mixing the milled grain with water and at least one enzyme selected from the group consisting of protease, alpha amylase, glucoamylase, cell wall degrading enzyme, and mixtures thereof, wherein the pH of the mixture is optionally adjusted to a pH of about 3.5 to about 6.5 (e.g., 3.5 to 6.5), and incubating the mixture for about 1 to about 3 hours (e.g., 1 to 3 hours) to produce an incubated mixture.

The processes may further involve separating the incubated mixture into germ and a liquid slurry, reducing the particle size of materials in the liquid slurry by grinding, adding yeast and amylase to the liquid slurry and fermenting for about 30 to about 72 hours (e.g., 30 to 72 hours), removing ethanol from the liquid slurry (e.g., by distillation) and separating (e.g., screening) the liquid slurry into fiber and a defibered liquid slurry, and separating (e.g., centrifuging) the defibered liquid slurry to produce protein solids.

The process may further involve separating the incubated mixture into germ and a liquid slurry, reducing the particle size of materials in the liquid slurry by grinding, adding amylase to the liquid slurry to hydrolyze the starches in the liquid slurry, and separating (e.g., screening) the liquid slurry into fiber and a defibered liquid slurry, and separating (e.g., centrifuging) the defibered liquid slurry into protein solids and a solution containing sugars.

The process may further involve separating the incubated mixture into germ and a liquid slurry, reducing the particle size of materials in the liquid slurry by grinding, adding amylase to the liquid slurry and heating (e.g., about 60 to about 130° C. (60-130° C.), preferably about 75 to about 105° C. (75-105° C.)) for about 15 min to about 2 hours (e.g., 15 min to 2 hours) (liquefaction), adding glucoamylase enzyme to the liquid slurry to hydrolyze the starches in the liquid slurry (saccharification), and separating (e.g., screening) the liquid slurry into fiber and a defibered liquid slurry, and separating (e.g., centrifuging) the defibered liquid slurry into protein solids and a solution containing sugars.

Utilizing a dry grinding system, corn (or other grains) can be ground so that the germ is not broken or damaged. This can be done using tempered or untempered grain; tempering generally is conducted at about 60° C. or below for about 15 minutes to about 3 hours. The grain is then mixed in water at a temperature below the gelatinization temperature of the starch (the gelatinization temperature of corn starch is typically about 70° C. but it can be higher or lower depending on the specific type of corn used; generally the range could be as low as 62° C. and as high as 78° C.), and the pH adjusted to the active range of the specific enzyme(s) being used. The grain is then incubated for a period of about 1 to about 6 hours (e.g., 1 to 6 hours) so that the specific gravity of the suspension is sufficient for the germ to float and be recovered. If the specific gravity is sufficiently increased, the coarse fiber could also float and be recovered with the germ. This recovery could be done using hydrocyclones or by floatation. Once the germ (and potentially the coarse fiber) has been removed, the particle sizes of the remaining solids in the slurry are reduced in size using an appropriate grinding device. The slurry can then be further incubated and or treated with other enzymes and used to produce several different products.

The general ethanol production process is well known in the art. Ethanol can be made by incubating with either native starch degrading enzymes or with thermostable starch degrading enzymes along with an elevated temperature treatment above the gelatinization temperature of the starch. The solution is then fermented with yeast to produce ethanol. After fermentation, the ethanol is removed by distillation. Following distillation, the fine fiber is recovered using fine mesh screens. The insoluble protein and yeast cells can then be recovered separately from the liquid stream by centrifugation or fine filtration such as vacuum belt filtration or micro filtration membranes. Non-germ oil can optionally be recovered using a high-speed centrifugation.

Starch can be isolated if the enzyme used is a protease that can break down the protein matrix surrounding the starch granules, and the finely ground slurry is further incubated to release the starch granules (Enzymatic Wet Milling process). Following this treatment, the slurry can then be separated using standard wet milling separation systems for starch, gluten and fiber recovery.

A sugar solution may also be prepared by treating with a combination of native starch degrading enzymes under temperature and enzyme combinations that can hydrolyze the starch and release glucose, maltose or a combination of oligosaccharides from starch hydrolysis. Following this hydrolysis, the fiber and insoluble protein can be separated as above and the fiber and insoluble protein washed to remove residual sugars. The sugar solution can then be utilized for ethanol production or other purposes. The solution can also be treated to remove the insoluble protein by centrifugation or fine filtration such as vacuum belt filtration or micro filtration membranes.

Utilizing this system, corn or other grains (e.g., sorghum, wheat, barley, rye and triticale) can be enzymatically processed without the need for soaking the grain prior to grinding. This will save significantly on capital cost for implementation and reduce processing times.

"Optional" or "optionally" means that the subsequently described event or circumstance may or may not occur, and that the description includes instances in which said event or circumstance occurs and instances where it does not. For example, the phrase "optionally comprising a defoaming agent" means that the composition may or may not contain a defoaming agent and that this description includes compositions that contain and do not contain a foaming agent.

By the term "effective amount" of a compound or property as provided herein is meant such amount as is capable of performing the function of the compound or property for which an effective amount is expressed. As will be pointed out below, the exact amount required will vary from process to process, depending on recognized variables such as the compounds employed and the processing conditions observed. Thus, it is not possible to specify an exact "effective amount." However, an appropriate effective amount may be determined by one of ordinary skill in the art using only routine experimentation.

Unless defined otherwise, all technical and scientific terms used herein have the same meaning as commonly understood by one of ordinary skill in the art to which the invention belongs. As used herein, the term "about" refers to a quantity, level, value or amount that varies by as much as 10% to a reference quantity, level, value or amount. Although any methods and materials similar or equivalent to those described herein can be used in the practice or testing of the present invention, the preferred methods and materials are now described.

The following examples are intended only to further illustrate the invention and are not intended to limit the scope of the invention as defined by the claims.

Examples

Materials and Enzymes: The enzymes used were gifts of DuPont Industrial Biosciences (Palo Alto, Calif.). SPEZYME RSL® (thermostable α-amylase), OPTIDEX® L-400 (glucoamylase), PROSTEEP® (a protease), and FERMGEN® (an acid protease) were all commercially available products and used by volume with the activities as defined by the manufacturer. The Red Star Ethanol Red yeast was a gift from Lesaffre (Milwaukee, Wis.). Urea was from IBI Scientific (Peosta, Iowa). Corn was #2 yellow dent commodity corn grown during the 2014 crop year.

Corn Grinding and Analysis: Corn was ground for germ recovery experiments without tempering using a custom-built degermination mill; however, commercially available mills (off the shelf) could readily be used. The mill utilized a rotary impact grinding mechanism surrounded by a screen with 9.65 mm (0.38") diameter round holes. The mill is described in detail by Brekke, O. L., et al. (Cereal Chemistry 48(5): 499-511 (1971)). Our mill was built at the USDA Eastern Regional Research Center, Wyndmoor, Pa.

For experiments without germ recovery, corn was ground using a Bunn (Springfield, Ill.) model G2 burr mill coffee grinder. The gap was set so that the ground corn produced would pass through a 1 mm screen.

The fermentations were done using 553 grams of corn that was weighed prior to grinding and the entire amount collected directly into the tared beakers. A smaller quantity of the same corn was ground and collected for moisture determinations. Moisture content was determined each day and for each grinding method used according to AOAC Official Method 930.15 (AOAC International, 2005). The measured dry weights were used for all mass balance and yield determinations.

Conventional Mash Preparation with Additional Particle Size Reduction: The ground corn (still containing the corn germ but is ground intact) was mixed with water in a tared 2 L beaker and the total slurry weight adjusted to 1500 grams. The particle size of the slurry was further reduced using an IKA (Wilmington, N.C.) T25 Disperser with an 18G dispersing element at 16,000 rpm for 3 to 5 min until the slurry was uniform. A mechanical mixer was used and the pH adjusted to 5.8 using 1 N HCl. Alpha amylase (SPEZYME RSL®) was added at 0.5 mL/kg mash and the slurry heated on a hot plate and held for 60 min at 95° C. The mechanical mixer speed was adjusted as necessary as the slurry viscosity changed to maintain a well-mixed slurry. The mash was cooled in a water bath to 30° C. and supplemental N (400 ppm) added as urea. The pH was adjusted to 4.5 with 1 N HCl and glucoamylase (OPTIDEX® L-400) was added at a dosage of 0.4 mL/kg mash. Active yeast was added (Red Star Ethanol Red; 1.1 g/kg of mash) to start the fermentation and the entire slurry transferred into a tared 2 L Erlenmeyer flask. An acid protease (FERMGEN®) was added at 0.67 ml/kg of mash and the total slurry weight was then readjusted to 1500 g with water to compensate for evaporation losses. Small amounts of water for rinsing were required throughout the processing for probe and mixer rinsing and for final transfer to the incubation flask; however, these were less than what was lost through evaporation while heating. The flask was stoppered and a 21-gauge needle inserted to vent $CO_2$ produced.

Germ Recovery Mash Preparation: The degerminated ground corn (with intact corn germ) was mixed with water in a 2 L beaker and the pH adjusted to 4.5 using 1 N HCl. PROSTEEP® was added at 0.67 g/kg of mash and the total slurry weight adjusted to 1500 grams. The beaker was then incubated in a water bath at 48° C. and mixed with a mechanical mixer for 2 hours. Following incubation, the beaker was removed and the floating germ recovered by skimming using a small section of 2 mm wire screen (#10 mesh). The slurry was periodically mixed to allow more germ to float and again skimmed. This was done repeatedly until no more germ could be recovered (about 20 min). The germ was rinsed with 100 mL of water and the rinse water added to the degermed slurry. The germ collected was dried at 55° C. in a forced air oven. The degermed corn slurry was readjusted to 1500 g with water and processed without adjusting the pH (now about pH 4.9). The particle size of the slurry was further reduced using an IKA (Wilmington, N.C.) T25 Disperser with an 18G dispersing element at 16,000 rpm for 3-5 min until the slurry was uniform. A mechanical mixer was used and Alpha amylase (SPEZYME RSL®) was added at 0.5 mL/kg mash and the slurry heated on a hot plate and held for 60 min at 95° C. The mechanical mixer speed was adjusted as necessary as the slurry viscosity changed to maintain a well-mixed slurry. The mash was cooled in a water bath to 30° C. and supplemental N (400 ppm) added as urea. Glucoamylase (OPTIDEX® L-400) was added at a dosage of 0.4 mL/kg of mash. Active yeast was added (Red Star Ethanol Red; 1.1 g/kg of mash) to start the fermentation and the entire slurry transferred into a tared 2 L Erlenmeyer flask. The total slurry weight was then readjusted to 1500 g with water to compensate for evaporation losses. Small amounts of water for rinsing were required throughout the processing for probe and mixer rinsing and for final transfer to the incubation flask; however, these were less than what was lost through evaporation while heating. The flask was stoppered and a 21-gauge needle inserted to vent $CO_2$ produced.

Fermentation Rate and HPLC Analysis: Flasks were incubated in a New Brunswick Scientific Innova® 44 incubator at 30° C. with shaking at 200 rpm. Flasks were periodically removed and weighed to determine the weight loss due to $CO_2$ production and for fermentation rate analysis. Flasks were incubated for up to 72 hours. A small sample was taken at the end of the fermentation for HPLC determination of maltodextrins (DP4+), maltotriose (DP3), maltose, glucose, fructose, succinic acid, lactic acid, acetic acid, glycerol, methanol, and ethanol (Johnston, D. B. and A. J. McAloon, Bioresource Technology, 154: 18-25 (2014)). The starch content of the corn was measured using AACC Method 76-13 (AACC International 2000) and used to determine ethanol yields.

Fiber, Protein and DDGS Recovery: Following fermentation, the entire contents of the flask were transferred to a 2 L beaker and heated to 85° C. with mixing to remove the ethanol. Following ethanol removal, the fiber was recovered by screening through a 325 mesh (45 micron) screen (Dual manufacturing Co. Chicago, Ill.). The fiber was dewatered on the screen as much as possible by pressing with a spatula. No washing of the fiber was done at this stage. The volume of the screened stillage was measured, a sample taken for total solids analysis and then transferred into centrifuge bottles. The bottles were centrifuged in a bench top centrifuge at 2000×g for 10 min. The bottles were decanted and the volume of liquid measured and again a sample was taken for total solids analysis. The pellet of primarily insoluble protein and yeast cells was recovered from the centrifuge bottles and transferred with a small amount of DI water used for rinsing into tared weigh boats and dried at 55° C. The recovered fiber was mixed with the stillage and the mixture was freeze dried to produce a DDGS equivalent. Fermentations not requiring protein recovery were freeze dried after the ethanol removal step.

A washing procedure was also evaluated where the decanted liquid was added back to the fiber and rescreened through the 325 mesh screen. The liquid was then centrifuged again and the recovered pellet added to the protein solids. This was repeated two additional times followed by a 500 mL water wash.

Compositional Analysis: Moisture analysis was done according to AOAC Official Method 930.15. Protein was determined by combustion analysis according to AOAC 99.03. Crude lipid was determined using AOAC 945.16 or as described in Johnston et al. 2005 using a Dionex ASE extractor (AOAC International, 2012). Fiber analysis (ADF and NDF) was done using an ANKOM fiber analyzer and the manufacturer standard protocols. Crude Fiber was done using AOCS approved procedure Ba 6a-05. Starch was analyzed using AACC 76-11 with a YSI analyzer for glucose determination. All conditions and analytical testing were done in duplicate and results reported as averages.

Results and Discussion. Process Development and Grinding Characterization: Preliminary fermentation experiments were conducted using degermination ground corn and compared with conventional grinding. The results showed slow fermentations that took up to 5 days to reach completion. Ethanol yields were found to be significantly reduced when compared to the conventionally ground corn at 72 hours. These experiments led to the implementation of the secondary size reduction step using a wet grind process shown in FIG. 2A. This was also incorporated in the conventional process to eliminate any variation due to the added particle size reduction.

Figure 1:
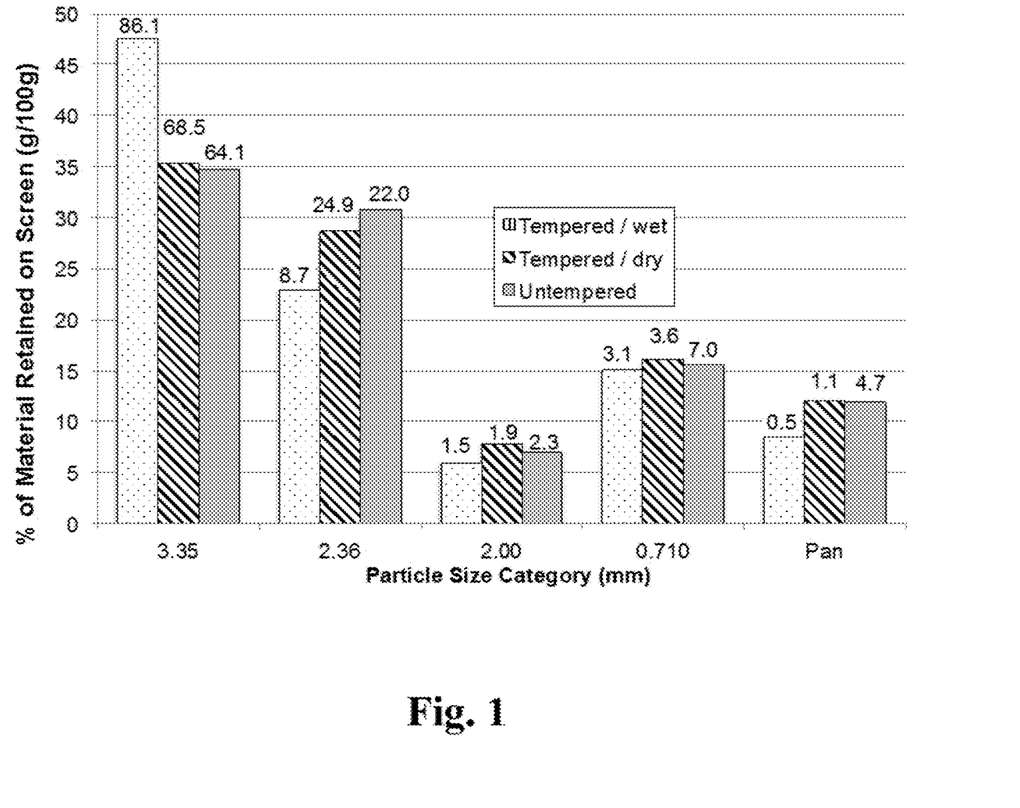
FIG. 1 shows particle size analysis of corn ground using a degermination mill for untempered (shaded), ground after tempering and sized wet (dotted), and ground after tempering and dried (diagonal stripes) prior to sizing as described below. Bars are averages of duplicate milling runs and data labels represent the percent of total oil content for each fraction.

In dry milling, tempering of the corn kernels (which raises the moisture content of the kernel) is done prior to grinding. This aids in the separation and fractionation of the components. Since our use of the mill was only to break the kernels without damaging the germ, we conducted all of our fermentations and recovery experiments without tempering; however, a comparison was done to evaluate the oil content of fractions with and without tempering and for particle size analysis. FIG. 1 shows the particle distribution for corn ground untempered (as used in germ recovery experiments), tempered and sieved undried (wet), and tempered and dried before sieving. Sieves having 3.35, 2.36, 2.00, 0.710 mm openings and pan (#6, 8, 10, 25, and pan) were chosen to differentiate larger particle sizes. Tempering was done at 60° C. for 60 minutes. The final moisture content was found to be 25.75% for the tempered corn and 12.76% for the untempered corn. The particle distribution clearly shows that the grind was much coarser than typically used in commercial ethanol facilities (Rausch, K. D., et al., Transactions of the ASAE, 48(1): 273-277 (2005)). Over 70% of the fractions were 2 mm or larger whereas typically over 85% would pass through this screen. The tempered corn had noticeably larger pieces of pericarp fiber relative to the untempered sample.

Batches of 100 kernels were ground and hand sorted in order to visually evaluate germ quality. No intact kernels and primarily intact germ with little apparent damage were surprisingly found. Undamaged germ is important for retaining the oil content within the germ during wet fractionation. Oil is known to be present outside of the germ in other parts of the kernel; however, the majority of oil in the kernel is located inside of the germ (80-85%; Watson, S. A., Description, Development, Structure, and Composition of the Corn Kernel, IN Corn chemistry and Technology, P. A. White and L. A. Johnston, 2003, pp. 69-106).

The sized fractions were analyzed for oil content and the percent of total kernel oil for each fraction is shown in FIG. 1 as data labels at the top of the bars. The results indicate that more than 85% of the total kernel oil was present in the two largest size fractions (>2.36 mm) that visually contain the intact germ. The tempered sample, that was fractionated prior to drying, showed 86.1% of the total oil in the >3.35 mm fraction with only 8.7% in the >2.36 mm fraction. When the tempered corn was dried after grinding prior to sieving, the oil content of the two largest fractions surprisingly more closely matched the untempered corn samples. This surprisingly indicated that the germ was still primarily intact, when ground with or without tempering using this type of mill and had the potential to be recovered in the germ fraction. It should be noted that the untempered fractions did have a larger percentage of oil in the two smallest fractions relative to either tempered sample, possibly indicating some germ being damaged.

Preliminary experiments were also done to evaluate the incubation time and the protease enzyme dose required for optimal germ recovery. Incubation times from 1-6 hours, temperatures from 40-60° C., and enzyme doses from 0.5-6 g/kg of corn were examined for germ recovery yields. It was surprisingly found that acceptable germ yields were reached by incubating for 2 hours at 48° C. with 2 g/kg of enzyme. Oil concentrations could be somewhat improved using longer incubation times; however, this complicated experimentations due to overall processing time. Lower pH and higher temperatures allowed reduced enzyme dosing but required base addition for raising the pH after germ recovery or the alpha amylase used was not sufficiently active. The future use of a low pH alpha amylase would be of significant benefit as no additional pH adjustment would be required.

It is important to note that many other types of enzymes, not just protease, could be utilized for the germ recovery process. In U.S. Pat. No. 6,899,910 (Johnston & Singh (2005)), we demonstrated that a range of enzymes could be utilized to hydrolyze endogenous components and alter the specific gravity to allow germ recovery. These other types of enzymes include amylases, proteases, and cell wall degrading enzyme or mixtures of these enzymes as well as other enzymes that could hydrolyze endogenous components to increase the specific gravity.

Figure 2A:
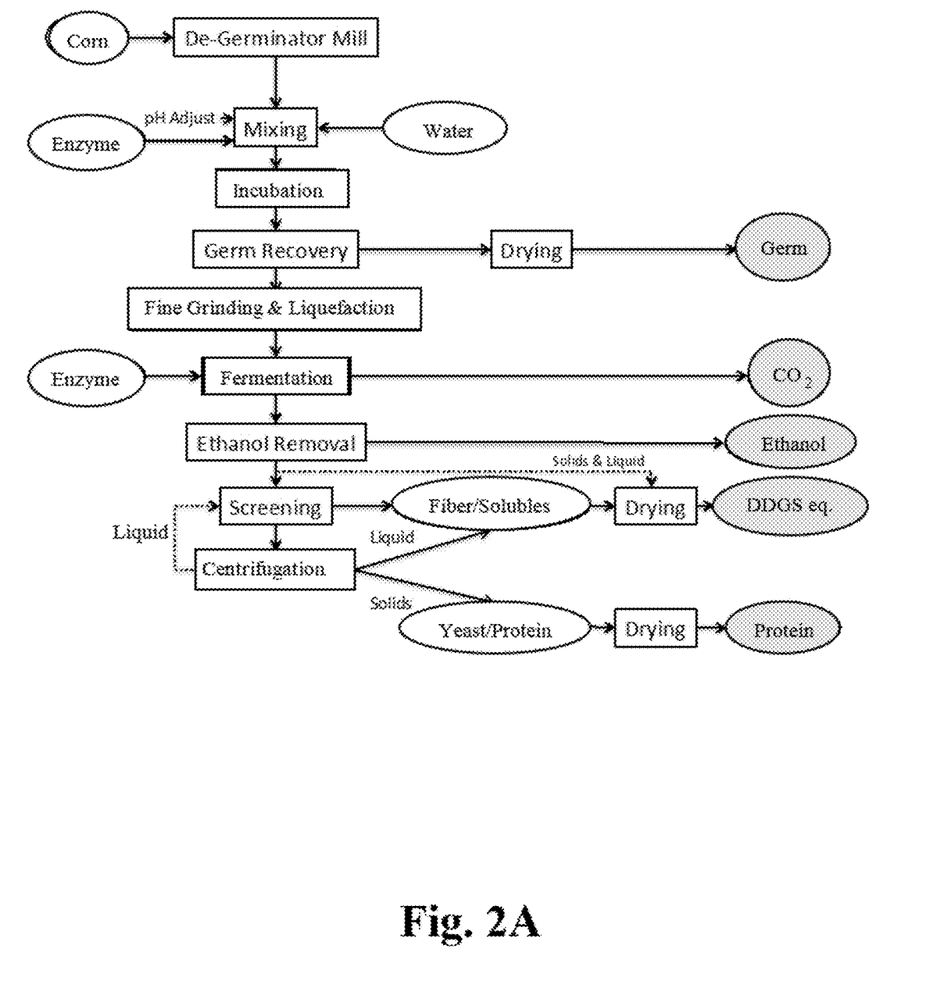
FIG. 2A and FIG. 2B are flow charts showing major steps for the degermination process and the conventional process as described below. Inputs are shown on the left and outputs on the right.
Figure 2B:
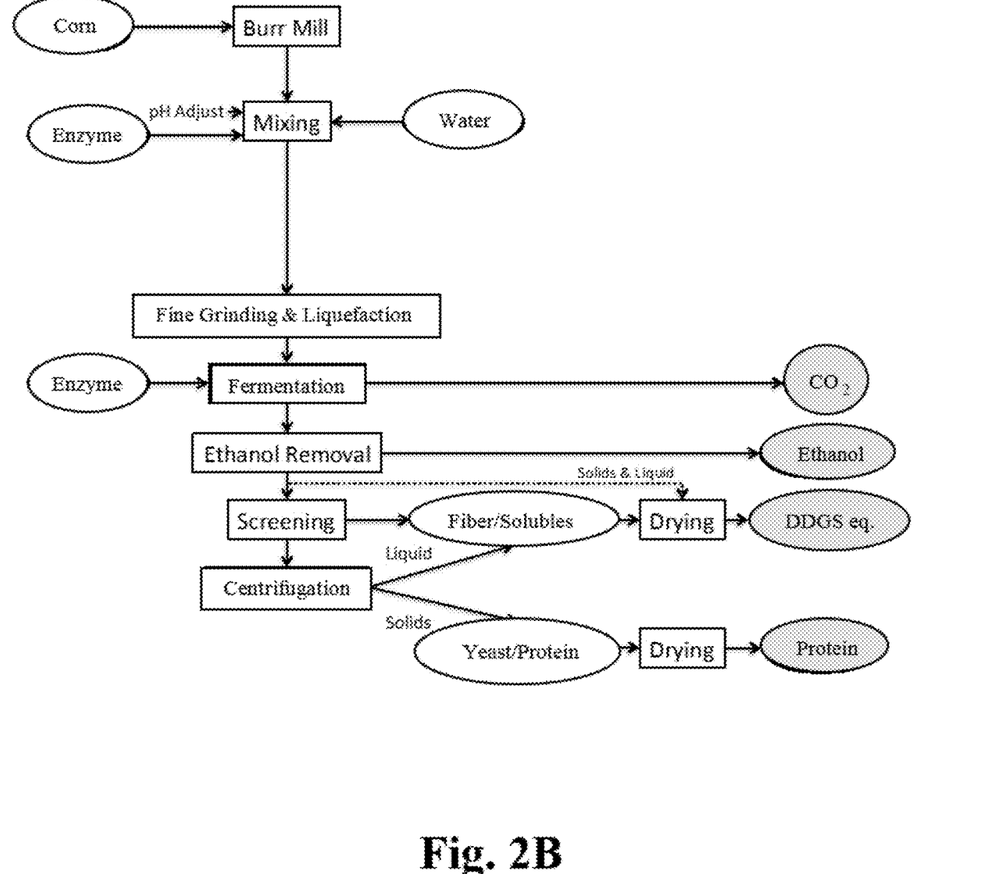

Process Description: FIG. 2A shows the germ recovery processing flow used for experiments and FIG. 2B shows the conventional process used when germ was not recovered. Each also shows the alternative process where conventional DDGS or Degermed DDGS are produced without fiber screening or protein recovery.

Fermentation Rate Comparison: Previous research has shown that fermentation rates and ethanol yields can be affected by the addition of protease during fermentation (Johnston and McAloon 2014; U.S. Pat. No. 5,231,017 (1991): Wang et al., Cereal Chem. 84(1): 10-14 (2007)). The process being described here also incorporated a secondary grinding that significantly reduced the particle size relative to the normal process and could surprisingly result in altering the rate and/or yield. To eliminate this as a variable, the secondary grinding step was also incorporated into the conventional process shown in FIG. 2B.

Figure 3:
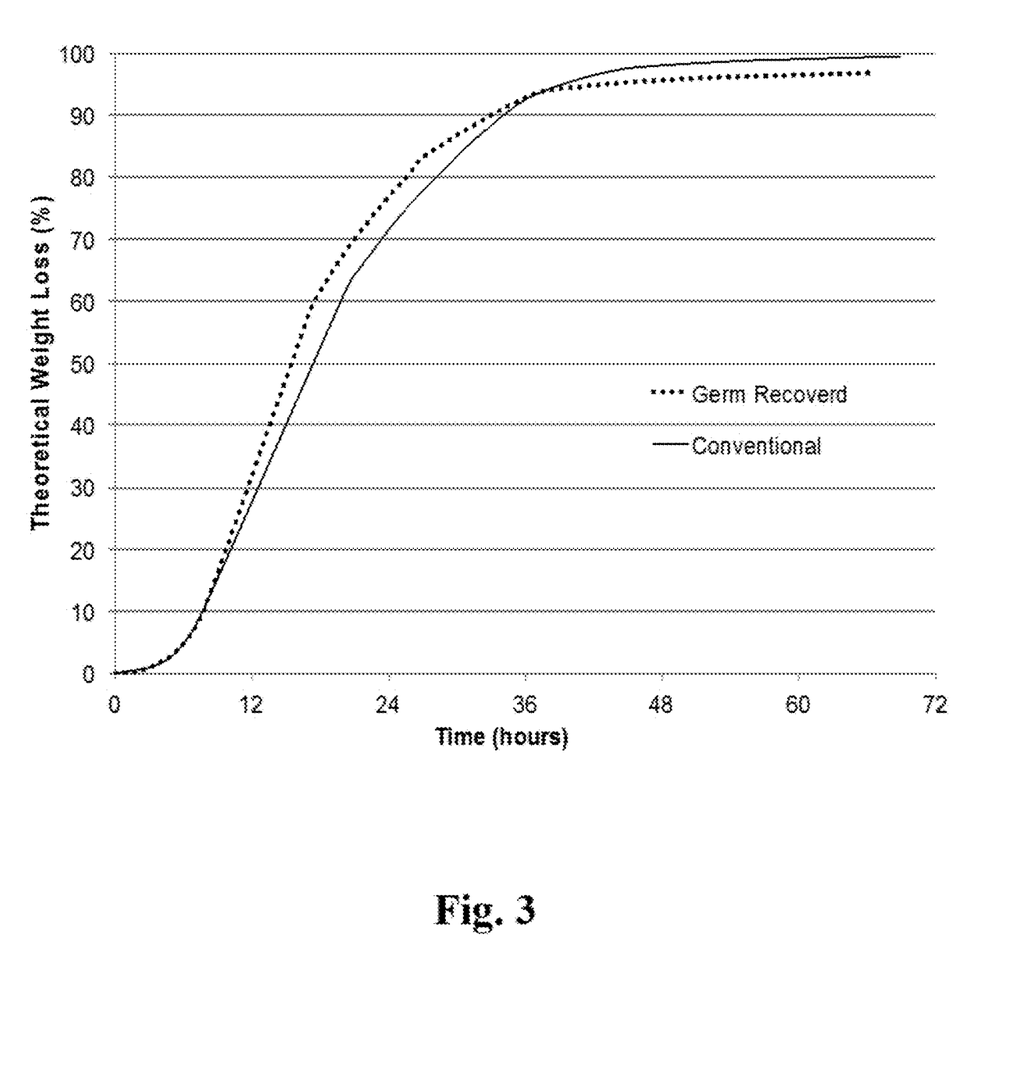
FIG. 3 shows average theoretical weight loss for fermentation done with germ recovery (dotted line) and for conventional fermentations (solid line) as described below.

Following the weight loss of the flasks over time was done to compare the fermentation rates and for overall mass balance. FIG. 3 shows the average weight loss curves for the conventional process and for our germ recovery process (dotted curve) as a percentage of the theoretical. Our germ recovery process surprisingly initially fermented somewhat faster relative to the conventional process; this is partially the result of reduced solids in the fermentation flask due to germ removal. Final weight loss using the germ recovery step was surprisingly only reduced by 2.3% relative to the conventional process where germ was still present during fermentation; this was likely due to some starch being lost with the germ fraction. Additional washing of the germ could reduce this loss; however, it was not possible with the laboratory scale batch process without significantly reducing the final solids content. In a continuous operating ethanol plant, the process condensate could first be used to wash the germ prior to being added to the ground corn. Some starch loss with germ recovery will be unavoidable but surprisingly it could potentially be as low as 1%.

Fraction Yields: The average germ recovery yield using protease was surprisingly found to be 8.06% of the starting corn on a dry weight basis. Preliminary trials using lower concentrations of protease reduced yields or required longer incubation time. This recovery value was surprisingly consistent with values for germ recovery yields from wet milling as well as other wet fractionation processes (Johnston et al. 2005; Eckhoff, S. R., et al., Cereal Chemistry, 70(6): 723-727 (1993); Ramirez, E. C., et al., "Enzymatic corn wet milling: Engineering process and cost model," Biotechnology for Biofuels, 2(2): article no. 2 (2009); Singh et al. 1996; Singh, V., et al., Cereal Chem., 82: 187-190 (2005))). Alpha amylase (Spezyme RSL) was also tested for germ recovery in place of the protease. Germ recovery surprisingly was slightly reduced to 7.2% in these experiments; however, conditions were not optimized and yield could likely be improved. Using the alpha amylase prior to liquefaction would surprisingly remove the additional cost for protease.

Surprisingly the time needed for germ recovery was significantly less than needed for other wet fractionation processes (generally about 2 hours, shorter times could work by increasing the amount of enzyme used, but the germ is not as high a quality, fewer solubles leach out of the germ and as a consequence the oil content is reduced). Conventional corn wet milling requires 24-36 hours of steeping, quick germ utilizes up to 12 hours of soaking, and the E-Mill process utilizes up to 6 hours of combined soaking and incubation before germ can be recovered (Blanchard, P. H., Technology of Corn Wet Milling and Associated Process, 1992, Industrial Chemistry Library, Elsevier, Amsterdam, The Netherlands; Singh et al. 1996, 2005). Conventional dry milling (dry fractionation) is faster; however, the low oil concentration of the germ, the high starch loss, and reduced fermentation rates make it a less desirable process.

Figure 4:
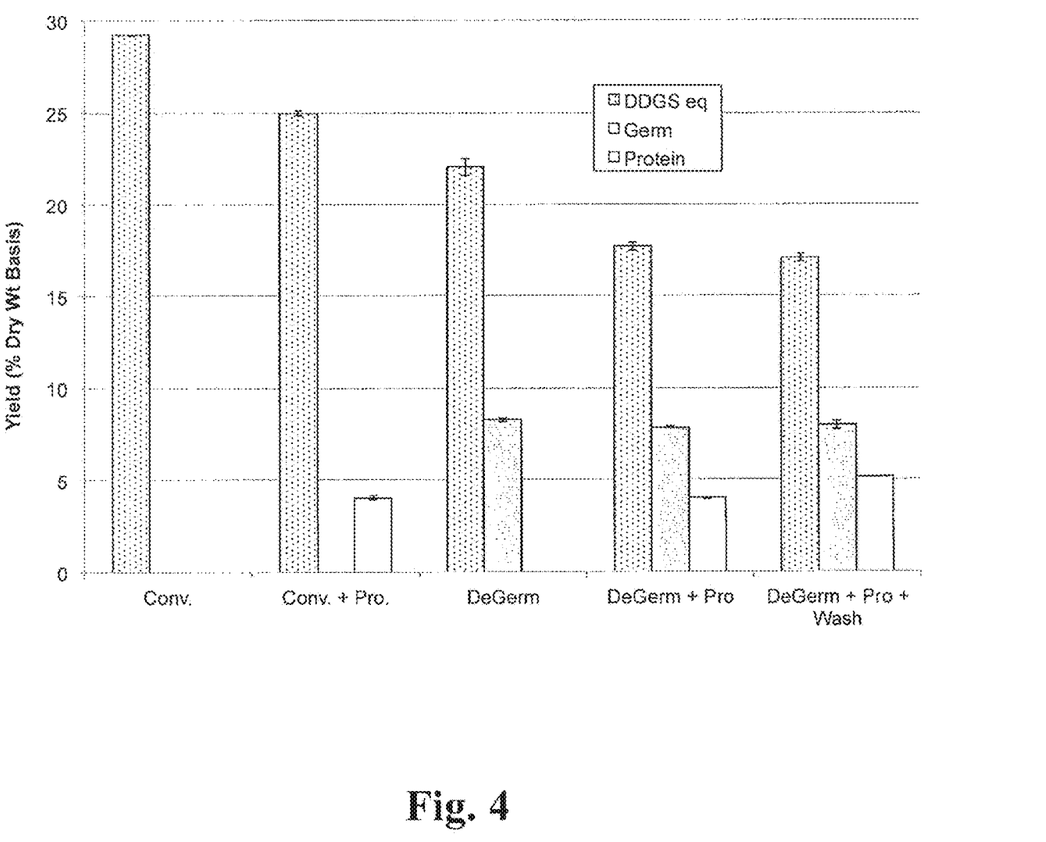
FIG. 4 shows fraction yields for components relative to starting corn as described below. The DDGS equivalents (dotted), Germ (dark shaded) and protein fractions (light shaded) are shown as the averaged values made on a dry weight basis. Error bars represent ±one standard deviation of the average.

Fiber recovery was done in conjunction with germ recovery, with protein recovery, and with germ and protein recovery to compare yields and final composition. The solubles recovered were added to the fiber fraction to produce DDGS equivalents. The yields were compared with control values without recovery of germ or protein and the yields are shown in FIG. 4. Surprisingly germ removal alone reduced the DDGS equivalent yield 24.5% relative to the control and protein recovery alone reduced the yield 14.5%. The combined removal of germ and protein surprisingly reduced the yield 39.4% relative to the control. Washing of the fiber as described above surprisingly resulted in an additional decrease of 2% reaching a 41.5% reduction in DDGS equivalents relative to the control. Surprisingly there was a corresponding increase in the protein fraction.

The post-fermentation recovery of fiber surprisingly reduced the amount of starch lost relative to previous processes that implemented fiber recovery prior to fermentation; however, it does not increase fermenter space because the fiber is still present during fermentation (by removing things prior to fermentation (as with up front germ recovery) the amount of non-fermentable material going into the fermenter is reduced thereby increasing fermenter space). Surprisingly germ recovery prior to fermentation in the current process did significantly increase fermentation space and reduced the amount of fiber recovered after fermentation. Germ recovery also surprisingly reduced fiber washing and dewatering difficulties as well.

Surprisingly protein fraction yields were not significantly affected by the addition of germ recovery and were found to be 4.0% of the starting corn. The addition of a fiber wash using the clarified stillage after centrifugation and protein recovery surprisingly increased the final protein fraction by 25% to reach a total yield of 5.1%. This wash could easily be incorporated into a continuous process without the need for any additional water usage.

Figure 5A:
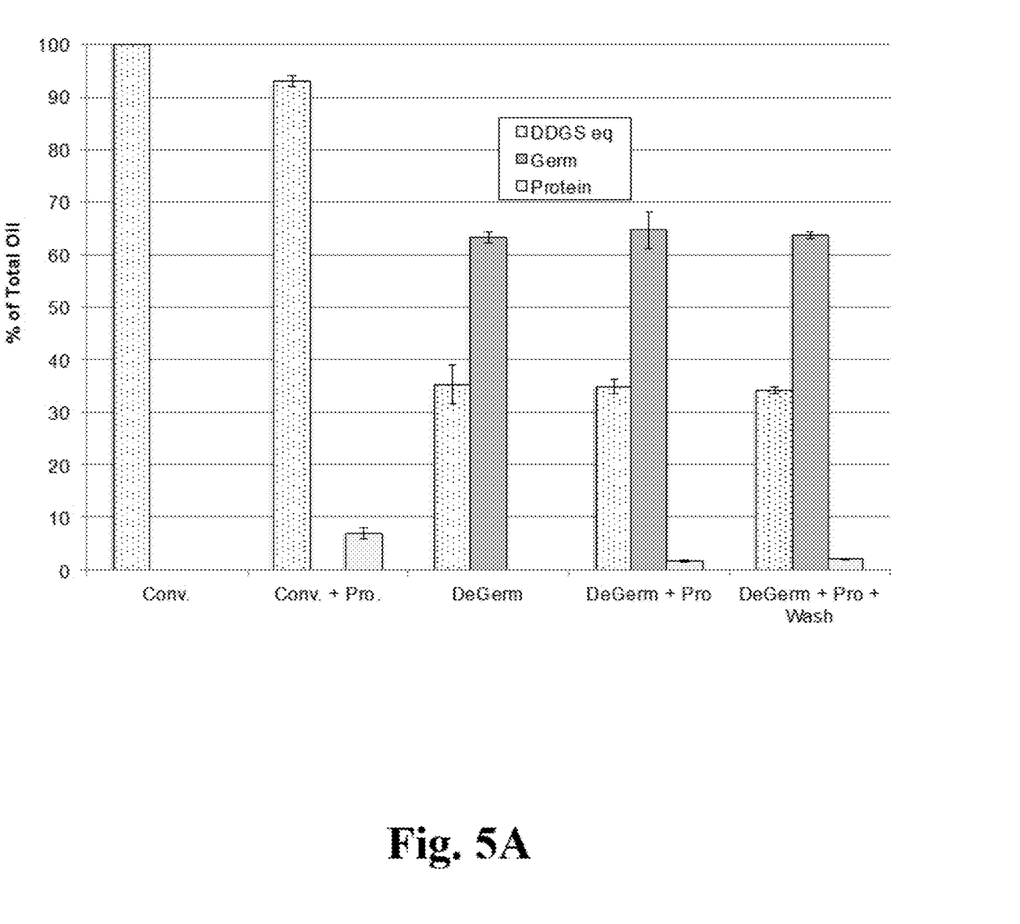
FIG. 5A shows oil yields for fraction relative to the total weight recovered and FIG. 5B shows protein yields for fraction relative to the total weight recovered as described below. The DDGS equivalents (dotted), Germ (dark shaded), and protein fractions (light shaded) are shown as the averaged values made on a dry weight basis. Error bars represent ±one standard deviation of the average.
Figure 5B:
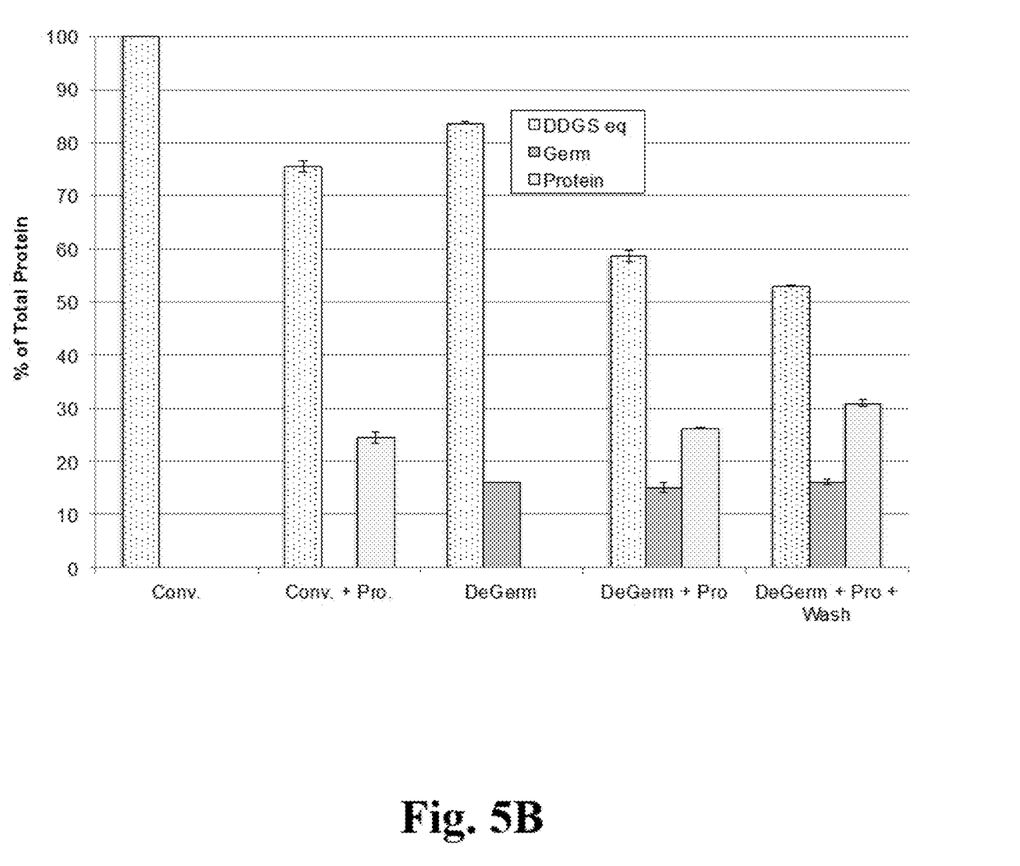

Compositional Analysis of Coproducts: Germ fractions, DDGS equivalents, and protein fractions were analyzed for protein and lipid content and compared in FIG. 5A and FIG. 5B as the percentage of the total recovered. The protein distribution (FIG. 5A) showed surprisingly that the majority of the protein remained with the DDGS equivalent fractions. The lowest amount of protein for the DDGS equivalent fractions was found when both the germ and protein fraction recovery was done and was reduced further with the addition of the washing step. The wash removed additional high protein yeast cells as well as insoluble protein from the fiber. The protein concentration for the recovered protein fractions ranged from 56.3 to 60.8% on a dry wt basis and was not found to be significantly different for any of the treatments. It is likely that the protein concentration may be altered if an alternative enzyme were used for germ recovery.

The lipid distribution (FIG. 5B) showed that the degermination process recovered approximately 65% of the total lipid in the germ fraction. This value was somewhat lower than expected given that published values indicate that 80-85% of the lipid is within the germ (Watson 2003). It is possible that the difference was due to solvent type or extraction efficiency for the different lipid components in the germ relative to the endosperm. It was also possible that some of the germ was not recovered in the floatation step or that germ was damaged in the grinding operation and oil leaked into the aqueous medium.

The DDGS equivalent fractions were also analyzed for fiber and other feed components and the averaged values are shown in Table 1 for the five conditions evaluated. The protein concentration of the DDGS equivalents was surprisingly increased relative to the conventional controls when germ was recovered; however, the oil content was reduced significantly. The degermed DDGS equivalents were reduced in oil concentration by about 50% relative to the controls. Surprisingly, except for the lipid content, the overall composition of the DDGS equivalent fractions were very similar to the conventional DDGS equivalents.

Overall Economic Evaluation: In order to estimate the economic value of our process, coproduct values and yields were compared between a 100 million gallon per year conventional facility and a facility producing our modified coproducts. The comparison of yields and values are shown in Table 2. The amount of corn utilized for the germ recovery process was greater relative to the conventional process due to the slightly lower ethanol yield and resulted in higher overall corn costs of $3.7 million. The overall value of coproducts was, however, surprisingly found to overcome the additional corn cost resulting in almost $17 million in additional revenue. Coproduct values were based on Midwest pricing given by the USDA Agricultural Market News for August 2015. The conventional DDGS value was $140/ton and our DDGS equivalent was estimated to be $95/ton or slightly lower due to reduced protein and lipid concentrations. Germ was estimated to be about $300/ton based on oil content and extraction costs as well as residual extracted meal value. The high protein fraction was estimated to be $450/ton and was based on the values of corn gluten meal ($550/ton) and soybean meal ($350/ton).

Detailed estimates of added operating expenses were not possible without the development of a full process model; however, we anticipate that these will surprisingly be less than 5¢ per gallon. Without the addition of added operating expenses, the additional revenue is surprisingly almost 16.70 per gallon of ethanol produced or about 45¢ per bushel processed; since the plants are large, this would be worth about $6 million per year at a 40 million gallon per year plant.

Conclusions: An enzyme based germ and fiber recovery process utilizing a modified milling strategy has been developed and demonstrated in a corn ethanol production process. The use of a protease was demonstrated to yield germ recoveries equivalent to conventional wet milling. Alpha amylase was also demonstrated to work for germ recovery; however, other enzymes should also work in this process if they can alter the specific gravity sufficiently. The ethanol yield decrease due to fractionation was surprisingly found to be less than 2.8% relative to conventional controls and could be reduced further using a continuous process. The DDGS equivalents produced have significantly reduced lipid content but slightly higher protein content. Reduced capital input and the high potential coproduct value should significantly improve the economic viability for this process relative to previous wet fractionation methods. Additionally, we have demonstrated that a variation of the milling process can be used to produce a sugar solution that can then be utilized in other processes, and another variation would allow for starch granules to be separated and recovered in a wet milling type operation.

Example for sugar solution: The degerminator ground corn was mixed with water in a 2 L beaker and the pH adjusted to 4.5 using 1 N HCl. PROSTEEP® was added at 0.67 g/kg of mash and the total slurry weight adjusted to give a solids concentration of 25% or 30% solids. The beaker was then incubated in a water bath at 48° C. and mixed with a mechanical mixer for 2 hours. Following incubation, the beaker was removed and the floating germ recovered by skimming using a small section of 2 mm wire screen (#10 mesh). The slurry was periodically mixed to allow more germ to float and again skimmed. This was done repeatedly until no more germ could be recovered (about 20 min). The germ was rinsed with 100 mL of water and the rinse water added to the degermed slurry. The germ collected was dried at 55° C. in a forced air oven. The degermed corn slurry was readjusted to 25% or 30% solids with water and processed without adjusting the pH (now about pH 4.9). The particle size of the slurry was further reduced using an IKA (Wilmington, N.C.) T25 Disperser with an 18G dispersing element at 16,000 rpm for 3-5 min until the slurry was uniform. A mechanical mixer was used and Alpha amylase (SPEZYME RSL®) was added at 0.5 mL/kg mash and a glucoamylase (OPTIDEX L 400) was added at 0.25 mL/kg mash the slurry incubated at 60° C. for 36 hours. Following incubation, the fiber could be recovered by screening and the residual solids (primarily insoluble protein) recovered by centrifugation. The remaining solution is the sugar solution. Table 3 shows the sugar concentrations (glucose, maltose, maltotriose and oligosaccharides of 4 glucose units or larger, (DP4+)) for the 25 and 30% solids preparations. In each case, the sugar concentrations produced indicates high yield.

This example utilized a starch hydrolysis procedure that does not gelatinize the starch first; however, that process could also be utilized effectively. This could be accomplished by incorporating a thermal treatment for gelatinization of the starch after addition of the alpha amylase but prior to addition of the glucoamylase. The glucoamylase would then be added after returning the slurry to 60° C. for incubation. The two processes are outlined generally in FIG. 2C and FIG. 2D.

All of the references cited herein, including U.S. Patents, are incorporated by reference in their entirety. Also incorporated by reference in their entirety are the following references: U.S. Pat. No. 7,829,680 (Sander, R. and L. D. Fritz (2010); U.S. Pat. No. 5,231,017 (Lantero, O. J. and J. J. Fish (1993)); Lopes, J. F., et al., Cereal Chemistry, 74(5): 633-638 (1997); AACC International, Approved Methods of Analysis, 11th Ed. (2000), AACC International, St. Paul, Minn., Method 76-13.01 and 76.11; AOAC, Official Methods of Analysis of AOAC International (2012), 19th Ed., AOAC International, Gaithersburg, Md., Methods 930.15, 990.03, 945.16, 942.05, and 985.01; AOCS, Official Methods and Recommended Practices of the AOCS, 5th ed. (1998), American Oil Chemists' Society Press, Champaign, Ill., Approved Procedure Ba 6a-05; Wang, P., et al., Cereal Chemistry, 82(6): 734-738 (2005).

Figure 2C:
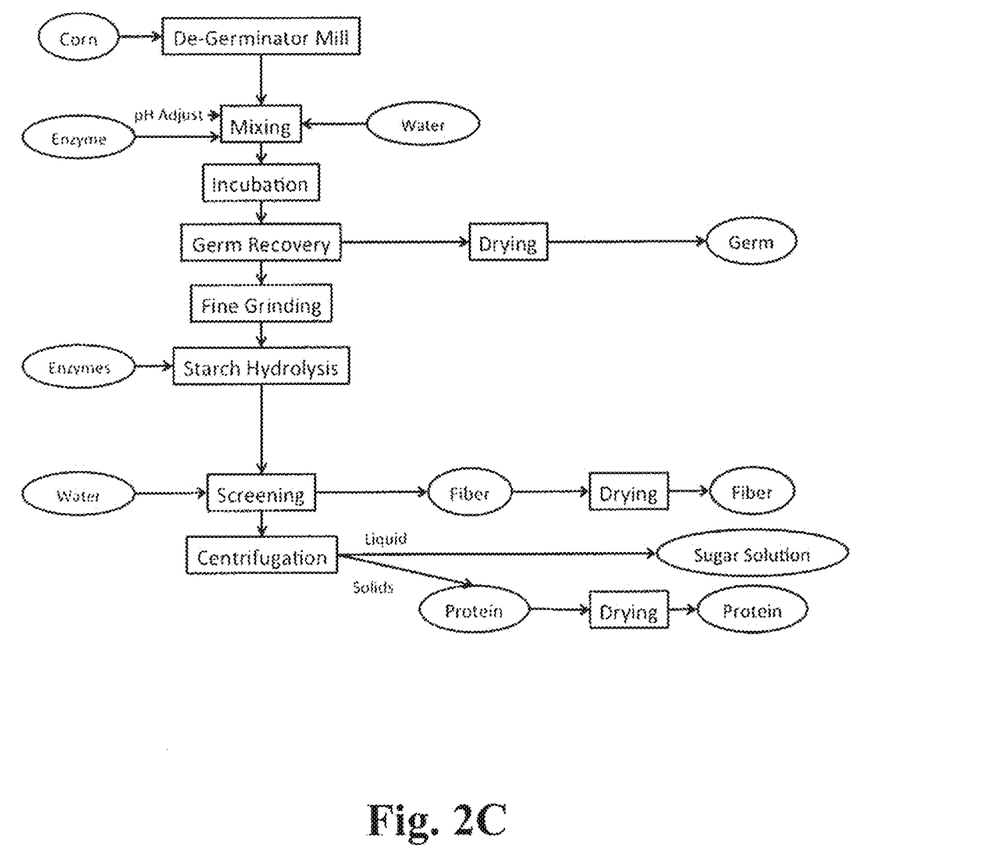

Thus, in view of the above, there is described (in part) the following:

A process of treating grain, said process comprising (or consisting essentially of or consisting of) milling said grain to produce milled grain wherein the grain germ remains intact in said milled grain, and producing a mixture by mixing said milled grain with water and at least one enzyme selected from the group consisting of protease, alpha amylase, glucoamylase, cell wall degrading enzyme, and mixtures thereof, wherein the pH of said mixture is optionally adjusted to a pH of about 3.5 to about 6.5 (e.g., 3.5 to 6.5), and incubating said mixture for about 1 to about 3 hours (e.g., 1 to 3 hours; preferably about 2 hours (2 hours)) to produce an incubated mixture (first part of FIG. 2C).

The above process, further comprising (or consisting essentially of or consisting of) separating said incubated mixture into germ and a liquid slurry, reducing the particle size of materials in said liquid slurry by grinding, adding yeast and amylase to said liquid slurry and fermenting for about 30 to about 72 hours (e.g., 30 to 72 hours), removing ethanol from said liquid slurry (e.g., by distillation) and separating (e.g., screening) said liquid slurry into fiber and a defibered liquid slurry, and separating (e.g., centrifuging) said defibered liquid slurry to produce protein solids (balance of FIG. 2A).

The above process, further comprising (or consisting essentially of or consisting of) separating said incubated mixture into germ and a liquid slurry, reducing the particle size of materials in said liquid slurry by grinding, adding amylase to said liquid slurry to hydrolyze the starches in said liquid slurry, and separating (e.g., screening) said liquid slurry into fiber and a defibered liquid slurry, and separating (e.g., centrifuging) said defibered liquid slurry into protein solids and a solution containing sugars (FIG. 2C).

Figure 2D:
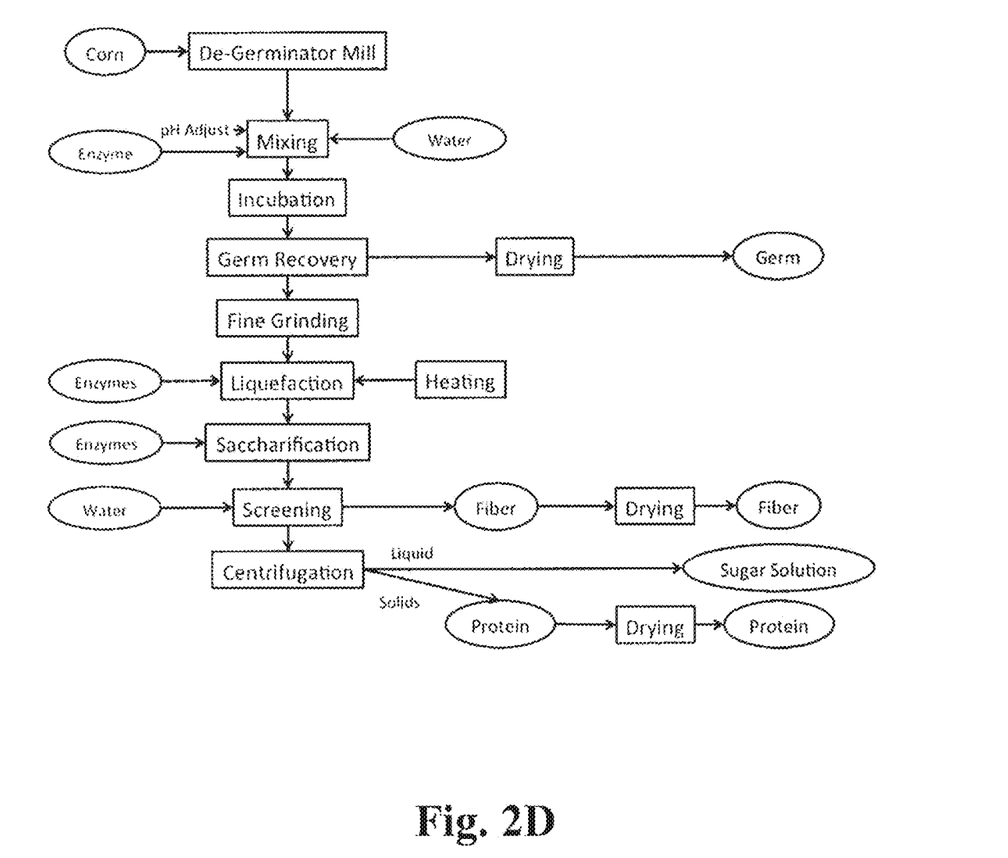

The above process, further comprising (or consisting essentially of or consisting of) separating said incubated mixture into germ and a liquid slurry, reducing the particle size of materials in said liquid slurry by grinding, adding amylase to said liquid slurry and heating (e.g. about 60 to about 130° C. (60-130° C.), preferably about 75 to about 105° C. (75-105° C.)) for about 15 min to about 2 hours (e.g., 15 min to 2 hours) (liquefaction), adding glucoamylase enzyme to said liquid slurry to hydrolyze the starches in said liquid slurry (saccharification), and separating (e.g., screening) said liquid slurry into fiber and a defibered liquid slurry, and separating (e.g., centrifuging) said defibered liquid slurry into protein solids and a solution containing sugars (FIG. 2D).

The above process, wherein said grain is corn.

The term "consisting essentially of" excludes additional method (or process) steps or composition components that substantially interfere with the intended activity of the method (or process) or composition, and can be readily determined by those skilled in the art (for example, from a consideration of this specification or practice of the invention disclosed herein).

The invention illustratively disclosed herein suitably may be practiced in the absence of any element (e.g., method (or process) steps or composition components) which is not specifically disclosed herein.

Other embodiments of the invention will be apparent to those skilled in the art from a consideration of this specification or practice of the invention disclosed herein. It is intended that the specification and examples be considered as exemplary only, with the true scope and spirit of the invention being indicated by the following claims.

TABLE 1

Average composition of fiber and DDGS fractions with and without protein fraction recovery[a]

| Component | Unit | Conventional | | De-Germinated | | |
|---|---|---|---|---|---|---|
| | | With | Without | With | Without | With + Wash |
| Protein (crude) | % | 27.8 ± 1.70 | 31.6 ± 1.41 | 31.4 ± 2.8 | 36.0 ± 2.12 | 25.5 ± 0.78 |
| Fat (crude) | % | 14.4 ± 0.21 | 13.4 ± 1.06 | 7.43 ± 0.8 | 5.92 ± 1.0 | 4.1 ± 0.25 |
| Fiber (acid detergent) | % | 9.3 ± 0.28 | 8.6 ± 1.70 | 10.9 ± 0.6 | 10.9 ± 0.14 | 11.0 ± 0.21 |
| Fiber (crude) | % | 5.9 ± 0.29 | 6.0 ± 0.42 | 7.0 ± 1.5 | 6.2 ± 0.03 | 8.6 ± 0.36 |
| Fiber (neutral detergent) | % | 32.0 ± 0.57 | 27.8 ± 0.21 | 38.0 ± 2.3 | 31.1 ± 1.27 | 35.2 ± 0.64 |
| Ash | % | 5.7 ± 0.18 | 5.4 ± 0.22 | 5.8 ± 0.2 | 5.6 ± 0.18 | 5.9 ± 0.04 |
| Hunter color L value | L Value | 76.3 ± 1.6 | 78.4 ± 1.3 | 76.4 ± 1.1 | 80.4 ± 0.21 | 75.5 ± 0.85 |
| Total digestible nutrients | Mcal/lbs | 92.9 ± 0.6 | 91.7 ± 1.7 | 84.1 ± 0.14 | 81.8 ± 0.57 | 79.5 ± 0.28 |
| Net energy (lactation) | Mcal/lbs | 1.0 ± 0.01 | 1.0 ± 0.02 | 0.88 ± 0.00 | 0.86 ± 0.01 | 0.8 ± 0.00 |
| Net energy (maint.) | Mcal/lbs | 1.0 ± 0.01 | 1.0 ± 0.02 | 0.92 ± 0.00 | 0.89 ± 0.01 | 0.9 ± 0.01 |
| Net energy (gain) | Mcal/lbs | 0.7 ± 0.00 | 0.7 ± 0.01 | 0.61 ± 0.00 | 0.60 ± 0.01 | 0.6 ± 0.00 |
| Digestible energy | Mcal/lbs | 1.9 ± 0.01 | 1.8 ± 0.04 | 1.68 ± 0.00 | 1.64 ± 0.01 | 1.6 ± 0.00 |
| Metabolizable energy | Mcal/lbs | 1.7 ± 0.01 | 1.6 ± 0.03 | 1.51 ± 0.01 | 1.45 ± 0.00 | 1.4 ± 0.01 |
| Sulfur (total) | % | 0.3 ± 0.01 | 0.3 ± 0.01 | 0.34 ± 0.01 | 0.39 ± 0.02 | 0.3 ± 0.01 |
| Phosphorus (total) | % | 1.2 ± 0.02 | 1.1 ± 0.02 | 1.08 ± 0.06 | 1.04 ± 0.06 | 0.9 ± 0.04 |
| Potassium (total) | % | 1.4 ± 0.00 | 1.3 ± 0.01 | 1.69 ± 0.06 | 1.53 ± 0.04 | 1.7 ± 0.06 |
| Magnesium (total) | % | 0.4 ± 0.01 | 0.4 ± 0.01 | 0.32 ± 0.01 | 0.3 ± 0.01 | 0.3 ± 0.01 |

TABLE 1-continued

Average composition of fiber and DDGS fractions with and without protein fraction recovery[a]

| Component | Unit | Conventional | | De-Germinated | | |
| --- | --- | --- | --- | --- | --- | --- |
| | | With | Without | With | Without | With + Wash |
| Calcium (total) | % | 0.0 ± 0.01 | 0.0 ± 0.01 | 0.01 ± 0.00 | 0.01 ± 0.00 | 0.04 ± 0.01 |
| Sodium (total) | % | 0.0 ± 0.01 | 0.0 ± 0.00 | 0.06 ± 0.00 | 0.06 ± 0.00 | 0.1 ± 0.01 |
| Iron (total) | ppm | 58.7 ± 1.34 | 71.4 ± 0.64 | 40.4 ± 2.40 | 50.1 ± 3.32 | 35.2 ± 2.62 |
| Manganese (total) | ppm | 17.8 ± 0.28 | 17.0 ± 0.42 | 12.3 ± 0.28 | 11.6 ± 0.57 | 10.5 ± 0.35 |
| Copper (total) | ppm | 23.7 ± 4.60 | 10.1 ± 3.04 | 31.7 ± 11.24 | 8.9 ± 0.71 | 39.5 ± 1.13 |
| Zinc (total) | ppm | 68.6 ± 1.63 | 65.2 ± 3.11 | 46.9 ± 5.73 | 40.1 ± 1.34 | 44.5 ± 0.64 |
| Starch (total) | % | 2.4 ± 0.42 | 2.5 ± 0.04 | 2.9 ± 0.14 | 2.4 ± 0.05 | 2.6 ± 0.02 |

[a]Analysis was partially done at a commercial lab for these fractions.

TABLE 2

Estimated Value of Coproducts for 100 Million Gallon Ethanol Facility[a]

| Component | Conventional | | | De-Germinated | | | Difference | |
| --- | --- | --- | --- | --- | --- | --- | --- | --- |
| | Yield | Lbs. | Value ($) | Yield | Lbs. | Value ($) | Lbs. | Value ($) |
| Corn | | 2,000,000,000 | $128,571,429 | | 2,057,613,169 | $132,275,132 | 57,613,169 | $3,703,704 |
| DDGS | 29.20% | 551,555,556 | $38,608,889 | 17.12% | 332,693,187 | $14,971,193 | −218,862,369 | −$23,637,695 |
| Germ | 0.00% | 0.0 | 0 | 8.01% | 145,173,671 | $21,776,051 | 145,173,671 | $21,766,051 |
| Protein | 0.00% | 0.0 | 0 | 5.10% | 99,108,368 | $22,299,383 | 99,108,368 | $22,299,383 |
| Ethanol | 2.80[b] | 100,000,000 | $150,000,000 | 2.72[b] | 100,000,000 | $150,000,000 | 0 | $0 |
| Output-Corn cost | | | $60,037,460 | | | $76,771,495 | | $16,734,034 |

[a]Estimates based on Corn ($3.6/bushel), DDGS ($140/ton), Ethanol ($1.50/gallon). Protein price used ($450/ton) was between Soybean meal ($350/ton) and Corn Gluten Meal ($550/ton). Corn Germ was based on crude oil price of ($0.41/pound) and germ oil content plus germ meal value.
[b]Ethanol yields per bushel for Conventional was 2.8 and 2.722 for De-Germinated.

TABLE 3

| | Solids Content | |
| --- | --- | --- |
| Sugar | 30% | 25% |
| DP4+ | 0.40 | 0.53 |
| Maltotriose | 0.51 | 0.55 |
| Maltose | 2.06 | 2.15 |
| Glucose | 24.25 | 18.73 |

We claim:

1. A process of treating grain, said process comprising dry milling said grain to produce milled grain wherein the grain germ remains intact in said milled grain, and producing a mixture by mixing at a temperature below the gelatinization temperature of starch said milled grain with water and protease and optionally at least one enzyme selected from the group consisting of alpha amylase, glucoamylase, cell wall degrading enzyme, and mixtures thereof, wherein the pH of said mixture is adjusted to a pH of 3.5 to 6.5, and incubating said mixture for about 1 to about 3 hours to produce an incubated mixture;

said process further comprising:
(a) separating said incubated mixture into germ and a liquid slurry, reducing the particle size of materials in said liquid slurry by grinding, adding yeast and amylase to said liquid slurry and fermenting for about 30 to about 72 hours, removing ethanol from said liquid slurry and separating said liquid slurry into fiber and a defibered liquid slurry, and separating said defibered liquid slurry to produce protein solids; or
(b) separating said incubated mixture into germ and a liquid slurry, reducing the particle size of materials in said liquid slurry by grinding, adding amylase to said liquid slurry to hydrolyze the starches in said liquid slurry, and separating said liquid slurry into fiber and a defibered liquid slurry, and separating said defibered liquid slurry into protein solids and a solution containing sugars; or
(c) separating said incubated mixture into germ and a liquid slurry, reducing the particle size of materials in said liquid slurry by grinding, adding amylase to said liquid slurry and heating for about 15 min to about 2 hours, adding glucoamylase enzyme to said liquid slurry to hydrolyze the starches in said liquid slurry, and separating said liquid slurry into fiber and a defibered liquid slurry, and separating said defibered liquid slurry into protein solids and a solution containing sugars wherein said process does not involve thermal gelatinization of starch prior to germ recovery.

2. A process of treating grain, said process comprising dry milling said grain to produce milled grain wherein the grain germ remains intact in said milled grain, and producing a mixture by mixing at a temperature below the gelatinization temperature of starch said milled grain with water and protease and optionally at least one enzyme selected from the group consisting of alpha amylase, glucoamylase, cell wall degrading enzyme, and mixtures thereof, wherein the pH of said mixture is adjusted to a pH of 3.5 to 6.5, and incubating said mixture for about 1 to about 3 hours to produce an incubated mixture;

said process further comprising separating said incubated mixture into germ and a liquid slurry, reducing the particle size of materials in said liquid slurry by grinding, adding yeast and amylase to said liquid slurry and fermenting for about 30 to about 72 hours, removing ethanol from said liquid slurry and separating said liquid slurry into fiber and a defibered liquid slurry, and separating said defibered liquid slurry to produce protein solids;

wherein said process does not involve thermal gelatinization of starch prior to germ recovery.

3. A process of treating grain, said process comprising dry milling said grain to produce milled grain wherein the grain germ remains intact in said milled grain, and producing a mixture by mixing at a temperature below the gelatinization temperature of starch said milled grain with water and protease and optionally at least one enzyme selected from the group consisting of alpha amylase, glucoamylase, cell wall degrading enzyme, and mixtures thereof, wherein the pH of said mixture is adjusted to a pH of 3.5 to 6.5, and incubating said mixture for about 1 to about 3 hours to produce an incubated mixture;

said process further comprising separating said incubated mixture into germ and a liquid slurry, reducing the particle size of materials in said liquid slurry by grinding, adding amylase to said liquid slurry to hydrolyze the starches in said liquid slurry, and separating said liquid slurry into fiber and a defibered liquid slurry, and separating said defibered liquid slurry into protein solids and a solution containing sugars;

wherein said process does not involve thermal gelatinization of starch prior to germ recovery.

4. A process of treating grain, said process comprising dry milling said grain to produce milled grain wherein the grain germ remains intact in said milled grain, and producing a mixture by mixing at a temperature below the gelatinization temperature of starch said milled grain with water and protease and optionally at least one enzyme selected from the group consisting of alpha amylase, glucoamylase, cell wall degrading enzyme, and mixtures thereof, wherein the pH of said mixture is adjusted to a pH of 3.5 to 6.5, and incubating said mixture for about 1 to about 3 hours to produce an incubated mixture;

said process further comprising separating said incubated mixture into germ and a liquid slurry, reducing the particle size of materials in said liquid slurry by grinding, adding amylase to said liquid slurry and heating for about 15 min to about 2 hours, adding glucoamylase enzyme to said liquid slurry to hydrolyze the starches in said liquid slurry, and separating said liquid slurry into fiber and a defibered liquid slurry, and separating said defibered liquid slurry into protein solids and a solution containing sugars;

wherein said process does not involve thermal gelatinization of starch prior to germ recovery.

5. The process of claim 1, wherein said grain is corn.

\* \* \* \* \*